United States Patent
Stradella et al.

(10) Patent No.: US 7,806,295 B2
(45) Date of Patent: Oct. 5, 2010

(54) DOSE INDICATOR FOR FLUID PRODUCT DISPENSING DEVICE

(75) Inventors: Fabio Stradella, Camogli (IT); Giuseppe Stradella, Camogli (IT)

(73) Assignee: Valois S.A.S, Le Neubourg (FR)

( * ) Notice: Subject to any disclaimer, the term of this patent is extended or adjusted under 35 U.S.C. 154(b) by 834 days.

(21) Appl. No.: 10/564,315

(22) PCT Filed: Jul. 13, 2004

(86) PCT No.: PCT/FR2004/001844
§ 371 (c)(1),
(2), (4) Date: Dec. 21, 2006

(87) PCT Pub. No.: WO2005/017824
PCT Pub. Date: Feb. 24, 2005

(65) Prior Publication Data
US 2008/0041877 A1    Feb. 21, 2008

(30) Foreign Application Priority Data
Jul. 18, 2003    (FR) .................................. 03 08833

(51) Int. Cl.
*B67D 7/22* (2010.01)
(52) U.S. Cl. ..................... 222/36; 128/205.23
(58) Field of Classification Search .................. 222/30, 222/32, 36, 22, 39–49, 162; 128/200.14, 128/200.17, 200.23, 200.12, 200.15, 205.23, 128/200.18, 200.24; 215/230; 116/306, 116/309
See application file for complete search history.

(56) References Cited

U.S. PATENT DOCUMENTS

| 5,421,482 | A | * | 6/1995 | Garby et al. ................... 222/36 |
| 5,611,444 | A | * | 3/1997 | Garby et al. ................. 215/230 |
| 5,718,355 | A | * | 2/1998 | Garby et al. ................... 222/36 |
| 5,799,651 | A | * | 9/1998 | Garby et al. ........... 128/200.23 |
| 6,679,251 | B1 | * | 1/2004 | Gallem et al. .......... 128/200.23 |
| 6,769,601 | B2 | * | 8/2004 | Haikarainen et al. ...... 235/87 R |
| 6,997,349 | B2 | * | 2/2006 | Blacker et al. ................ 222/23 |
| 7,191,918 | B2 | * | 3/2007 | Ouyang et al. ................ 222/36 |

(Continued)

FOREIGN PATENT DOCUMENTS

GB    1336014    *    6/1970

(Continued)

*Primary Examiner*—Lien T Ngo
(74) *Attorney, Agent, or Firm*—Sughrue Mion, PLLC (57) ABSTRACT

The invention relates to a dose indicator (A) which is intended for a fluid product dispensing device (B). The inventive indicator consists of at least one rotary counting means (10) which can move in rotation and which comprises indicator means (15), said indicator means indicating the number of doses that have been distributed or that remain to be distributed. Moreover, said at least one counting means is actuated by an actuation member (35) which is in turn actuated by a transmission element (34) that is designed to co-operate with a part (54) of the dispensing device (B) each time the latter is actuated. The dose indicator further comprises adjustment means (134) which are disposed between the transmission element (34) and the aforementioned part (54) of the dispensing device (B) and which can be moved and/or deformed, such that, during the assembly of the dispensing device (B), the distance at rest between the transmission element (34) and said part (54) of the dispensing device (B) can be precisely pre-determined.

31 Claims, 4 Drawing Sheets

U.S. PATENT DOCUMENTS

| | | |
|---|---|---|
| 7,195,134 B2 * | 3/2007 | Ouyang et al. ................ 222/36 |
| 2007/0235027 A1 * | 10/2007 | Schuckmann .......... 128/200.17 |
| 2008/0210230 A1 * | 9/2008 | Lintern et al. .......... 128/200.23 |

FOREIGN PATENT DOCUMENTS

| | | |
|---|---|---|
| GB | 1 317 315 A | 5/1973 |
| GB | 2 372 542 A | 8/2002 |
| WO | WO 00/09187 A1 | 2/2000 |
| WO | WO 01/37909 A1 | 5/2001 |
| WO | WO 0137909 A1 * | 5/2001 |

* cited by examiner

DOSE INDICATOR FOR FLUID PRODUCT DISPENSING DEVICE

BACKGROUND OF THE INVENTION (1) Field of the Invention

This present invention concerns a dose indicator, and a fluid-product dispensing device that includes such an indicator.

(2) Description of Related Art

In the area of fluid-product dispensing devices intended to dispense several doses, and in particular in the area of sprays, many systems have been developed that are intended to indicate the number of doses dispensed or the number of doses remaining to be.

Most of these systems have many disadvantages. Thus, they are generally designed with several toothed wheels forming gear trains whose number depends on the number of doses to be counted. As a consequence, these counters or indicators can become very complex and bulky, and therefore expensive to manufacture and to assemble. In addition, the indication is generally in the form of numbers which are often difficult for the user to read, in particular when the dispensing devices are intended to dispense a large number of doses, such as up to 200 doses for example. Likewise, not all the current counter or dose indicator systems can be used by people with sight problems, and in particular by blind people. Another major disadvantage is the fact that the existing counters generally require a procedure for the assembly of the dispensing device which is modified by the presence of the counter, and which therefore differs from the usual assembly procedure. This increases the complexity of the device, and consequently involves greater cost.

In addition, a very important safety requirement is to avoid any risk of under counting, that is not to count a total or partial dispensing of the product. In order to eliminate this risk, it is necessary that the actuation of the counter should be effected during the stroke of the dispensing member, in particular of the valve element or stem, which occurs before the beginning of product expulsion. The length of this initial stroke is generally very short, typically of the order of 1 to 1.5 mm, and the various dimensional tolerances of the device reduce the latter to a few tenths of millimeters. Such a short actuating stroke renders the actuation of the counter difficult, and can involve the use of complex mechanisms to guarantee functional counting.

Furthermore, some pumps or valves can be used to dispense doses of different volume, changing only the actuating stroke of the piston or of the valve element. It is then generally necessary to change the actuating means of the associated counters or indicators in order to adapt to the different strokes.

Document GB-1 317 315 describes a counter that includes means to compensate for the planned tolerances between the actuator of the counter and the body of the device housing said counter, these means being actuated after the first use of the device. This system is complex and not very reliable, since it actuates during the normal actuation of the device, and therefore more or less efficient according to the manner in which the user actuates the device.

BRIEF SUMMARY OF THE INVENTION

The present invention has as an objective to provide a dose indicator intended for a fluid-product dispensing device, which does not have the aforementioned disadvantages.

In particular, the present invention has as an objective to provide a dose indicator which is simple and inexpensive to manufacture and to assemble, and which can, in particular, be applied to all existing fluid-product dispensing devices without requiring modification of the assembly procedure.

The present invention also has as an objective to provide a dose indicator which is of small dimensions, independently of the number of doses contained in the dispensing device.

The present invention also has the objective of supplying a dose indicator which forms a complete and separate unit, and which, in particular, includes the actuating means of the indicator.

The present invention also has as an objective to provide a dose indicator which is easy for the user to read, and which can also be used by people with sight problems, and in particular by blind people.

The present invention also has as an objective to provide a dose indicator capable of compensating for manufacturing tolerances, in particular independently of the actuation and operation of the said indicator.

The present invention also has as an objective to provide a dose indicator which eliminates any risk of under-counting (no account taken of a distributed dose). More particularly, the present invention aims to provide a dose indicator which counts at the beginning of the actuating stroke of the dispensing member with which it is associated, even if this stroke is very short, independently of the manufacturing tolerances of the different components of the device, and independently of the total actuating stroke of the device.

The present invention therefore provide a dose indicator for a fluid product dispensing device, including at least one rotary counting means capable of being rotated, said at least one counting means including indicating means, showing the number of doses dispensed or remaining to be dispensed, said at least one counting means being actuated by an actuating member which itself is actuated by a transmission element suitable to cooperate with a part of the said dispensing device at each actuation of the latter, characterised in that the said dose indicator includes adaptation means located between said transmission element and said part of said dispensing device, said adaptation means being movable and/or deformable in order to accurately predetermine, during assembly of the dispensing device, the distance at rest between said transmission element and the said part of dispensing device.

Advantageously, said adaptation means includes a deformable and/or movable element attached to said transmission element, such as a peg, where the minimum force necessary to move and/or deform said element is greater than the force required to actuate the indicator, said element being deformed and/or moved only during assembly of the dispensing device.

Advantageously, said at least one rotary counting means includes a rotary counting wheel fitted with teeth, said teeth cooperating with actuating means that are suitable to turn said rotary wheel, where said actuating means include a flexible tab that includes a first flexible tab part and a second flexible tab part which is more rigid than the first tab part, the first tab part bearing an actuating tooth designed to cooperate with the teeth of said rotary counting wheel at each actuation of the device, and the second tab part supporting the transmission element suitable to cooperate with said fluid product dispensing device at each actuation of the latter, said flexible tab being attached to a ring surrounding said teeth, with said flexible tab cooperating with said teeth each time a dose is dispensed.

Advantageously, said ring includes non-return means, preventing said rotary disk from turning in the direction opposite to that induced by said flexible tab.

Advantageously, said ring includes a stop suitable to cooperate with a blocking element attached to said flexible tab so as to limit the rotation of said rotary counting wheel.

Advantageously, the more rigid second tab part is designed to flex from the moment when the blocking element is blocked by the stop means of the ring.

Advantageously, the rotation of the rotary counting wheel is effected at the beginning of the actuating stroke of the fluid-product dispensing device, with the flexing of the more rigid second tab part allowing continuation of said actuating stroke of the fluid-product dispensing device over its full distance despite the blocking of the blocking element by the stop means.

Advantageously, said transmission element is a shoulder attached to a flexible tab, and cooperating with a part of the fluid-product dispensing device which is movable during the actuation.

Advantageously, the indicator includes a linearly movable member which can be moved linearly, with the indicating means cooperating with a viewing opening provided in said linearly movable member, where the said at least one rotary counting means includes a rotary counting wheel with a hollow profile that cooperates with a projection of said linearly movable member, the shape of said hollow profile being such that at least some rotations of said rotary counting wheel result in a linear motion of said linearly movable member, changing the position of said linearly movable member in relation to said counting wheel.

Advantageously, said rotary counting wheel and said linearly movable member are placed in a cover which includes a viewing window that cooperates with the viewing opening of the linearly movable member.

Advantageously, the rotary counting wheel, the linearly movable member, the actuating means and the cover form a unit which can be assembled into a fluid-product dispensing device.

Advantageously, said indicating means follow said hollow profile at least partially.

Advantageously, the shape of said hollow profile is irregular so that the dose indication is progressive.

Advantageously, said hollow profile is at least partially in the shape of a spiral.

Advantageously, said indicating means are numbers and/or symbols.

Advantageously, said indicator includes amplification means, with the said amplification means converting linear movement of the transmission element into rotary movement of the actuating member, the projection in linear motion of said rotary movement being $\alpha.a$, where $\alpha>1$.

Advantageously, after assembly of the dispensing device, and in the rest position, the peg is placed at a distance "b" from the part of the dispensing device intended to actuate the indicator.

The present invention also provides a fluid-product dispensing device that includes a product reservoir, and a dispensing member, such as a pump or a valve, mounted on said reservoir, as well as a dose indicator as described above.

Advantageously, the dose indicator is actuated by a part of the dispensing device which is moved during the actuation of the device, and which cooperates with a transmission element of said indicator.

BRIEF DESCRIPTION OF THE DRAWINGS

Other characteristics and advantages of the present invention will appear more clearly from the following detailed description of one particular embodiment of the latter, given with reference to the attached drawings, which are provided by way of non-limited examples, and in which.

DETAILED DESCRIPTION OF THE PREFERRED EMBODIMENTS OF THE INVENTION

The dose indicator A of the present invention applies to all types of fluid-product dispensing devices. However, it applies more particularly to spray devices, and advantageously to aerosol devices that include a metering valve mounted on a receptacle or reservoir containing a product and a propellant gas.

Figure 1:
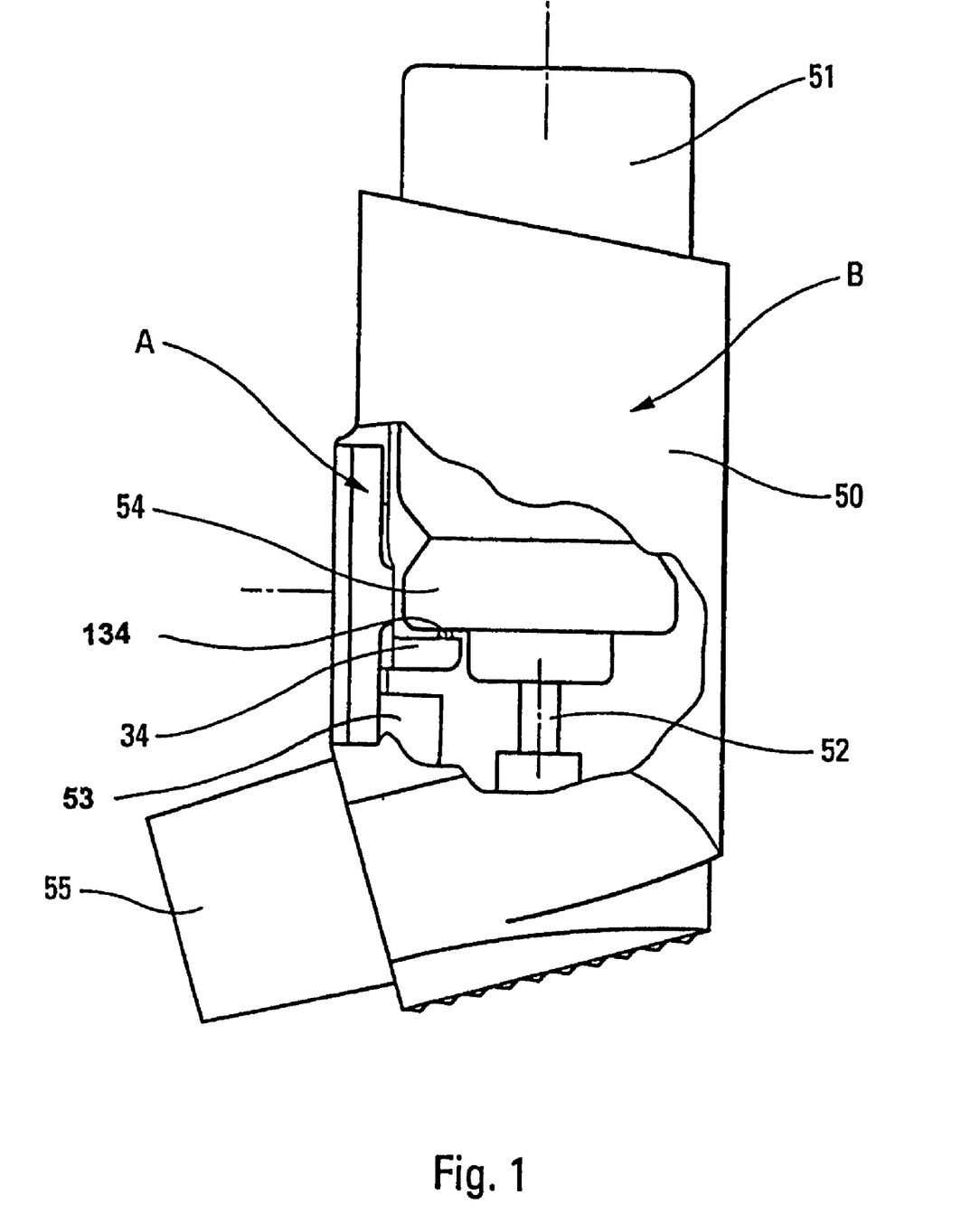
FIG. 1 is a schematic side view with partial cut-away, of a fluid-product dispensing device including a dose indicator according to one advantageous embodiment of the present invention.
Figure 2:
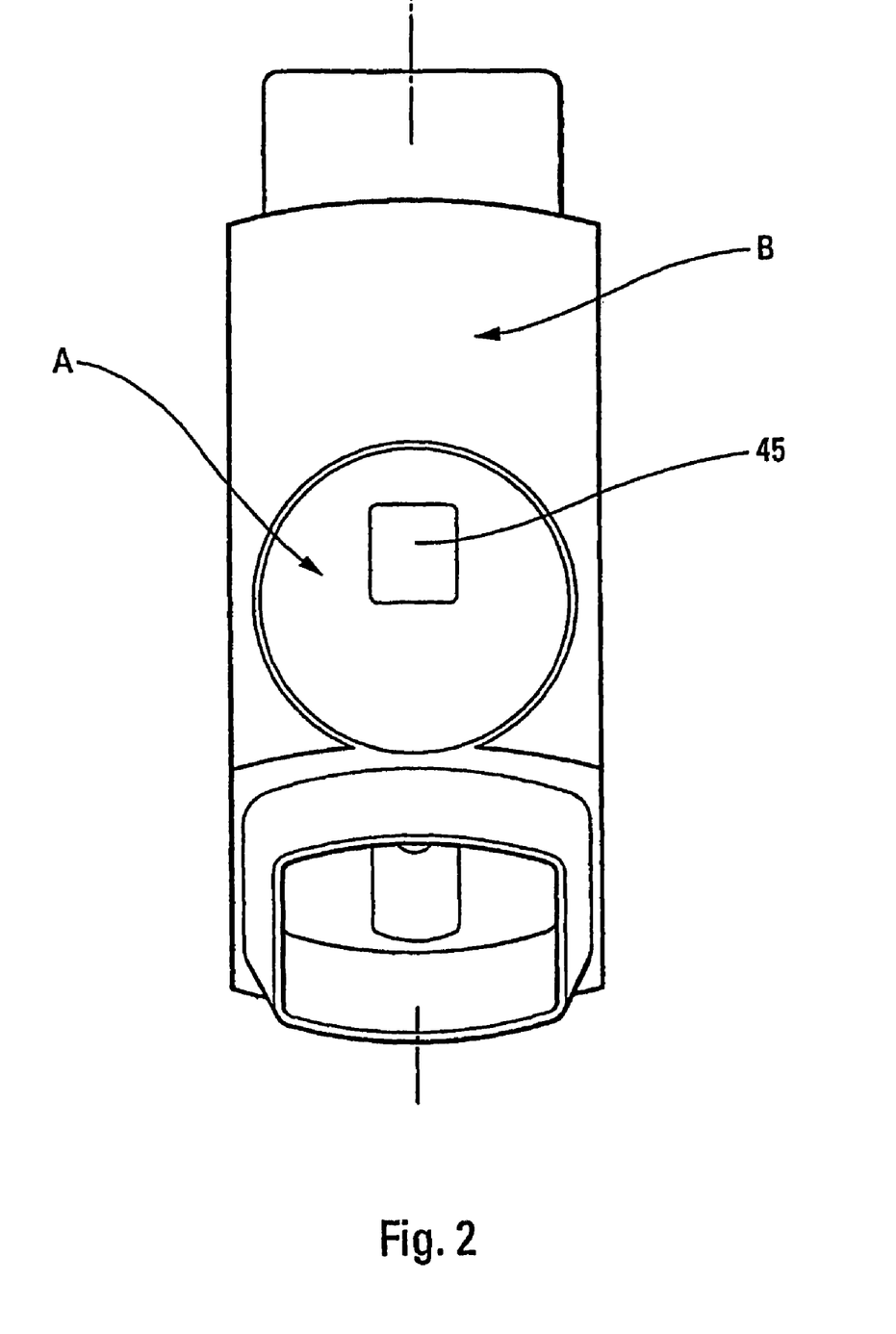
FIG. 2 is a front view, similar to that of FIG. 1.

FIGS. 1 and 2 schematically represent a dispensing device B for which the dose indicator A of the present invention is particularly well suited. This device includes a body 50 and a reservoir 51 on which a metering valve 52 is assembled. Since the actuation of the device B is obtained by axial movement of the reservoir 51 inside the body 50, this movement results in compression of the valve element or stem of the valve 52 which causes the expulsion of a quantity of product through an oral orifice 55. Of course, the present invention also applies to other types of dispensing device, and in particular to spray devices of the nasal type, or devices that have a pump in place of the valve.

Figure 3:
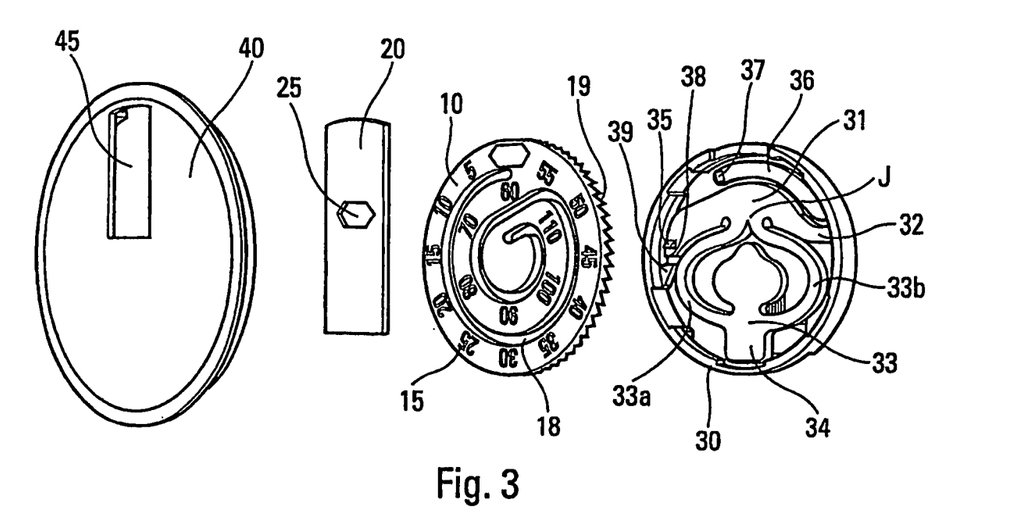
FIG. 3 is an exploded view of a dose indicator according to one advantageous embodiment of the invention.
Figure 4:
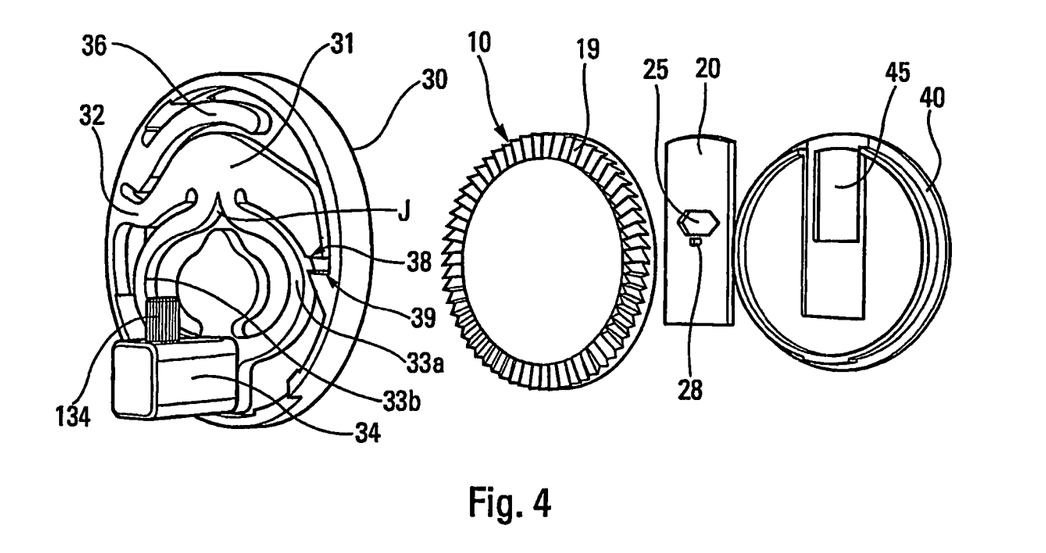
FIG. 4 is a view similar to that of FIG. 3, shown from another viewpoint.

FIGS. 3 and 4 represent a dose indicator A which can be used in particular with a fluid-product dispensing device B as described above. This dose indicator includes at least one rotary counting means which, in the example shown, is formed by a rotary counting wheel 10, preferably created in the form of a rotary disk, designed to rotate about an axis of rotation approximately perpendicular to said disk 10. This rotary disk 10 is preferably thin and made with a hollow profile 18, which can advantageously be made by means of a rib or groove. The disk 10 also advantageously includes a set of teeth 19, preferably positioned on its periphery, said teeth 19 being designed to cooperate with actuating means which are arranged to turn said disk 10, and which will be described more fully below. The disk or counting wheel 10 also includes indicating means 15, which can be numbers and/or symbols, and which are intended to indicate the number of doses dispensed or remaining to be dispensed. These indicating means 15 advantageously follow the said hollow profile 18 at least partially.

The indicator A shown in the figures can also advantageously include a linearly movable member 20, suitable to move in linear motion or translation. This linearly movable member 20 includes a projection 28, or any other equivalent means, which cooperates with the said hollow profile 18 of the rotary disk 10. This linearly movable member 20 is preferably made in the form of a thin plate, and includes a viewing opening 25 intended to open onto the indicating means 15 of the rotary disk 10.

Depending on the shape of the hollow profile 18, a rotation of the counting wheel 10 can result in a linear motion of the linearly movable member 20. Advantageously, the profile 18 is designed so that the indication is progressive and not regular. For example, the indicator of FIGS. 3 and 4 can count about 120 doses, with the last 50 being displayed in intervals of 5 in the viewing opening 25 of the linearly movable member 20, while the first doses are indicated in intervals of 10. In this example, the hollow profile 18 is firstly in a spiral, at the centre of the disk 10, so that each rotation of said disk 10 results in a linear motion of the said linearly movable member 20. When there remain only 50 doses to be dispensed, the profile 18 becomes cylindrical, so that the following rotations of the disk 10 no longer move the linearly movable member 20. The indicating numbers 18 then are shown in the viewing opening 25 as the device is actuated. After the last dose, a specific symbol 17 can indicate that there remains no dose to be dispensed. Other progressions can also be envisaged.

Advantageously, the counting wheel 10 and the linearly movable member 20 are placed in a cover 40, which is preferably also of thin design, and which includes a viewing window 45 that cooperates with the viewing opening 25 of the linearly movable member 20 in order to allow the user to view the indicating means 15 of the counting wheel 10.

The actuation of the indicator A, and in particular the rotation of the rotary counting wheel 10 can advantageously be brought about by actuating means incorporated into said indicator A. These actuating means can advantageously include a driving element 31 made in the form of a flexible tab, attached to a ring 30 which surrounds said teeth 19 of the rotary disk 10. This flexible tab 31 is designed to act on the said teeth 19 each time a dose is dispensed, preferably by means of an actuating member 35, such as a tooth. Advantageously, non-return means 36, 37 are provided in order to prevent said rotary disk 10 from turning in the reverse direction to that which is given to it by the flexible tab 31 during the actuation. These non-return means can include a flexible tab 36 bearing a non-return tooth 37 cooperating with the teeth 19.

The actuating means also include a transmission element 34 which is suitable to cooperate with the fluid-product dispensing device B at each actuation of the latter, with said transmission element 34 also cooperating with said flexible tab 31 in order to rotate said rotary disk 10. In particular, as seen in particular in FIG. 1, said transmission element 34 is a shoulder attached to the flexible tab 31 and which fits onto a part 54 of the fluid-product dispensing device B which is mobile during the actuation. In the example shown, it is ring 54 for securing the metering valve 52 onto the reservoir 51. Of course, and more generally, any part that moves during the actuation of the device B can be suitable to cooperate with the shoulder 34 so as to actuate the dose indicator A.

Figure 5:
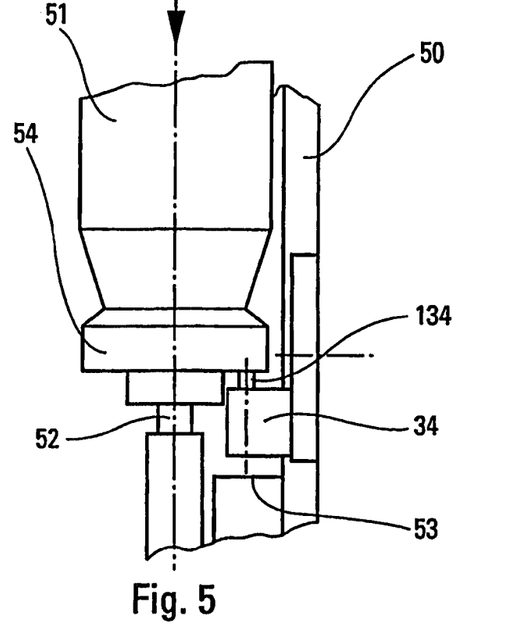
FIG. 5 is a schematic view of the adaptation means of the indicator of FIGS. 1 to 4, at the beginning of assembly of the reservoir of the dispensing device.
Figure 6:
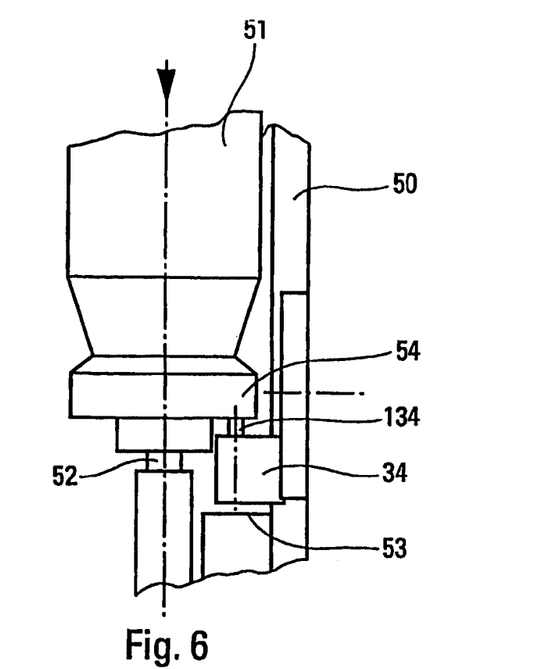
FIG. 6 is a view similar to that of FIG. 5, during the assembly process.
Figure 7:
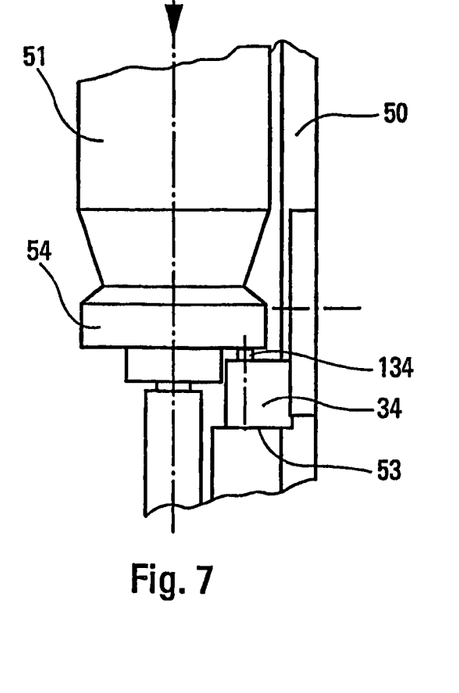
FIG. 7 is a view similar to that of FIGS. 5 and 6, at the end of assembly.
Figure 8:
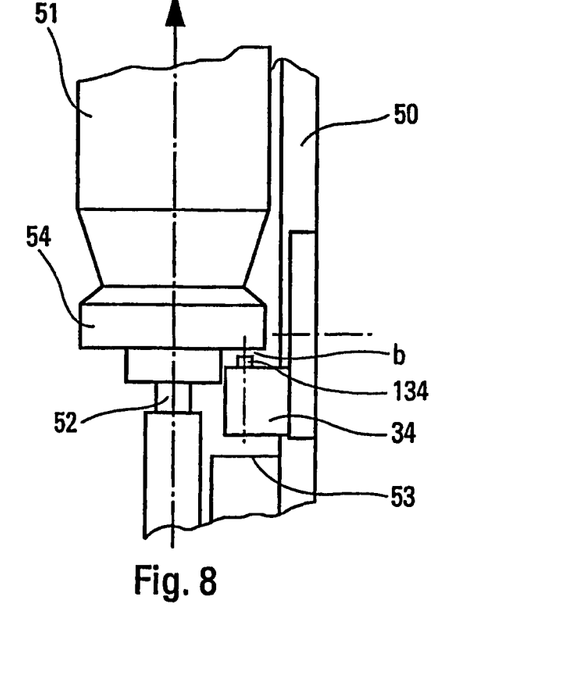
FIG. 8 is a view similar to that of FIGS. 5 to 7, after assembly, in the rest position of the device.

According to the invention, the indicator A includes adaptation means 134 allowing to compensate firstly for the manufacturing tolerances during the assembly of the dispensing device, and secondly for the various actuating strokes, such as for changing the dose volumes for example. More precisely, said adaptation means are used to predetermine the actuating stroke of the indicator A, by predetermining the distance, in the rest position, between the transmission element 34 and the part 54 of the device which cooperates with said transmission element 34 during the actuation. This distance is predetermined independently of the manufacturing or dimensional tolerances of the different parts making up the dispensing device B and the indicator A, and independently of the total actuating stroke of the dispensing device. To this end, the invention provides for adaptation means that are movable and/or deformable, placed between the transmission element 34 and the part 54. Advantageously, these adaptation means take the form of an adjustable peg 134 attached to the transmission element 34. Advantageously, this peg 134 can slide in said transmission element 34, and the force necessary to bring about this movement (and/or corresponding deformation) is greater than the force applied during the actuation of the device in order to dispense the product and to actuate the indicator A. The peg is therefore moved only during the assembly of the dispensing device B, and more particularly during the assembly of the reservoir 51, as seen in FIGS. 5 to 8. The body 50 includes a stop 53, and during the assembly process, the reservoir 51 (as well as any part 54 than can move with the reservoir 51) is pressed in as far as the actuating position of the valve element 52, with a force that is sufficient to move the peg. FIG. 5 shows the beginning of the assembly process. The reservoir firstly pushes the peg 134 and the transmission element 34 downwards in the figures, deforming the actuating means of the indicator A. FIG. 6 shows an intermediate position, where the transmission element 34 has moved, but the peg 134 has not moved in relation to said transmission element 34. At the end of its stroke, the bottom of the transmission element 34 comes up against the stop 53, and then the peg 134 is moved and/or deformed in relation to said transmission element 34 in order to adapt itself to the actuating stroke of the valve element 52. FIG. 8 shows the assembled device returned to the rest position, with the peg 134 in its adjusted position. During subsequent actuations of the device B, the peg no longer moves, since the force applied will no longer suffice. Only the assembly machine can cause the peg 134 to move. After assembly, the transmission element 34 and the peg 134 therefore form a single-block unit. As seen in FIG. 8, a safety distance "b" is specified in the rest position between the part 54 of the device B and the peg 134 (and therefore the transmission element 34). This can be obtained by fixing the distance between the stop 53 and the bottom of the transmission element 34 to a value that corresponds to the total actuating stroke of the valve element 52 less said safety distance "b". This distance "b" prevents any unplanned or undesirable actuation of the indicator. The adaptation means 134 therefore allow to predetermine the actuating stroke of the indicator A very precisely. The manufacturing tolerances, which, in particular, have an effect on the actuating stroke of the valve element, are compensated for by a more or less large movement of said adaptation means during assembly of the device. From the first actuation of the device, the indicator is therefore likely to function in a predictable and reliable manner.

In order to eliminate all risk of under-counting, it is desirable that the actuation of the indicator should occur at the beginning of the actuating stroke of the device B, before the expulsion of the dose begins. To this end, as seen in FIGS. 3 and 4, the flexible tab 31 can be provided with two flexible parts 32 and 33 of different flexibility, the first part 32 being more flexible than the second part 33. The second tab part 33 bears said shoulder 34, and when the spray device B is actuated, the securing ring 54 of the reservoir firstly drives the more flexible part 32 of the arm 31 to flex in parallel with the rotary disk 10, which causes the rotation of said disk 10 by means of the actuating tooth 35 which cooperates with the teeth 19. The flexible tab 31 advantageously includes a blocking element 38 suitable to cooperate with a projecting stop 39 attached to the ring 30. The radial distance between the blocking element 38 and the stop 39 advantageously corresponds to one tooth of the teeth 19. Thus, during actuation, the shoulder 34 is moved (downwards in the figures) by the dispensing device B, and the more flexible arm part 32 flexes (also downwards in the figures) until the blocking element 38 makes contact with the stop 39, as seen in FIG. 6. This results in rotation for the equivalent of one tooth of the counting wheel 10. The more flexible arm part 32 is then blocked, and continuation of the actuating stroke of the dispensing device B is possible by flexing of the less flexible arm part 33, as seen in FIG. 7. In this way, actuation of the dose indicator is able to occur in the first part of said actuating stroke. This eliminates all risk of not counting a dose that is dispensed (partially or totally) in the event of partial actuation of the dispensing device B, while still allowing continuation of the actuating stroke after counting. The stop 39 and the non-return means 36, 37 ensure that each dose is counted only once.

Advantageously, it is possible to provide amplification means suitable to amplify the movement of the transmission element 34 at the beginning of the actuating stroke, so that the movement of the actuating member (the tooth—35) is greater than the movement of said transmission element 34. To this end, the second tab part 33 can include a structure that is deformable elastically and which, in the drawings, is advantageously formed by two branches 33a and 33b. These branches are preferably convex, fixed firstly to the first tab part 32, and secondly to the transmission element 34. As seen in FIGS. 3 and 4, these branches 33a and 33b can former an ovoid structure with two opposed apex, one formed by said junction J, and the other formed by said transmission element 34. A movement of the transmission element 34 therefore causes a stretching of this ovoid structure, which pulls on the first tab part 32. The transmission element 34, and therefore the second tab part 33, moves in linear motion, while the first tab part 32 is rotated. The fact that the junction J is offset in relation to the axis of rotation of the first tab part 32 causes an amplification of the movement of the tooth 35, located on the other side of the junction J in relation to this axis of rotation. In the example shown, where the junction is approximately at the centre of the first tab part 32, the amplification factor is about 2. Of course by changing the position of the junction J, it is possible to change the amplification factor $\alpha$, though it will always be greater than 1. Advantageously, the second tab part 33 can be guided during its movement by appropriate means (not shown), positioned, for example, in the body 50 of the device. Advantageously, the branches 33a and 33b return elastically to their rest position after actuation. Other elastically deformable structures can also be envisaged.

The number of teeth in the tooth set 19 and the shape of the hollow profile 18 of the counting wheel 10 define the characteristics of the dose indicator, and in particular the number of doses that this indicator can count. The maximum number of doses and the display method can be varied as desired by changing the structure of the profile 18, the indicating means, or the number of teeth on the tooth set 19. The present invention therefore provides dose indicators that are capable of counting any number of doses, without altering the geometry or the size of said indicator. As mentioned previously, the dimensional structure of the present indicator is particularly small, in particular in terms of its thickness, and this indicator A can therefore be incorporated very easily into existing fluid-product dispensing devices B, as can be seen in FIGS. 1 and 2.

The dose indicator of the present invention can be used to display, in a simple, inexpensive and progressive manner, the number of doses dispensed or the number of doses remaining to be dispensed in the dispensing device. The structure of the indicator is very thin, independently of the number of doses that it has to indicate, and it includes no projecting part that involves modification of the device to which it is attached. As seen in FIG. 1, the doses indicator A of the present invention can be fitted very easily to any of the existing devices, without requiring that they be modified. Neither does the presence of the indicator A change the assembly process of the device B. The indicator can, for example, be installed in the device B through an opening provided for this purpose on the front part of the body 50 of the device. Another advantage of this present indicator is that the actuating means of the indicator are incorporated into the latter, so that the indicator forms an independent and separate unit which can be pre-assembled, and then incorporated easily into any fluid-product dispensing device. The dose indicator of the present invention ensures, in particular, the actuation of said indicator at the very start of the actuating stroke, in particular during the initial stroke which occurs before the beginning of expulsion of the dose. Whatever the length of this initial stroke, the adaptation means of the present invention allow compensation of any manufacturing tolerances, and therefore can be used to predetermine the length of the initial stroke, thus ensuring reliable counting.

Of course the present invention has been described with reference to one particular embodiment of the latter, as shown in the drawings, but it is not limited in any way to this particular form of implementation. On the contrary, anyone skilled in the art will be able to make all necessary modifications to it without moving outside the scope of the present invention, as specified in the appended claims.

The invention claimed is:

1. A dose indicator (A) for a fluid product dispensing device (B), including at least one rotary counting device (10) capable of being rotated, said at least one counting device including indicia (15) showing the number of doses dispensed or remaining to be dispensed, said at least one counting device being actuated by an actuating member (35) which itself is actuated by a transmission element (34) suitable to cooperate with a moving part (54) of said dispensing device (B) at each actuation of the dispensing device, wherein said dose indicator includes an adaptation device (134) located between said transmission element (34) and said moving part (54) of said dispensing device (B), said adaptation device (134) being movable, during assembly of the dispensing device (B), thereby setting a distance between said transmission element (34) and said moving part (54) to a predetermined distance when the dispensing device is in a rest position.

2. The indicator according to claim 1, in which said adaptation device (34) includes a movable element attached to said transmission element (34), the minimum force necessary to move said movable element (134) being greater than the force required to actuate the indicator, where said movable element is moved only during assembly of the dispensing device (B).

3. The indicator according to claim 2, in which said at least one rotary counting device includes a rotary counting wheel (10) fitted with teeth (19), said teeth (19) cooperating with actuating means (31, 34, 35) that are suitable to turn said rotary wheel (10), where said actuating means include a flexible tab (31) that includes a first flexible tab part (32) and a second flexible tab part (33) which is more rigid than the first tab part (32), the first tab part (32) bearing an actuating tooth (35) designed to cooperate with the teeth (19) of said rotary counting wheel (10) at each actuation of the device, and the second tab part (33) supporting the transmission element (34) suitable to cooperate with said fluid product dispensing device (B) at each actuation of the latter, said flexible tab (31)

being attached to a ring (30) surrounding said teeth (19), with said flexible tab (31) cooperating with said teeth (19) each time a dose is dispensed.

4. The indicator according to claim 3, in which said ring (30) includes non-return means (36, 37), preventing said rotary counting device (10) from turning in a direction opposite to that induced by said flexible tab (31).

5. The indicator according to claim 3, in which said ring (30) includes a stop (39) suitable to cooperate with a blocking element (38) attached to said flexible tab (31) so as to limit the rotation of said rotary counting wheel (10).

6. The indicator according to claim 5, in which the second, more rigid tab part (33) is designed to flex from the moment when the blocking element (38) is blocked by the stop means (39) of the ring (30).

7. The indicator according to claim 3, in which the rotation of the rotary counting wheel (10) is effected at the beginning of the actuating stroke of
the fluid product dispensing device (B), with the flexing of the second, more rigid tab part (33) allowing continuation of said actuating stroke of the fluid product dispensing device (B) for its full distance, despite the blocking of the blocking element (38) by the stop means (39).

8. The indicator according to claim 1, in which said transmission element (34) is a shoulder attached to a flexible tab (31), and cooperating with the moving part (54) of the fluid product dispensing device (B) which is movable during actuation of the dispensing device.

9. The indicator according to claim 1, in which the indicator (A) includes a linearly movable member (20) which can be moved linearly, with the indicia (15) cooperating with a viewing 15 opening (25) provided in said linearly movable member (20), where said at least one rotary counting device includes a rotary counting wheel (10) with a hollow profile (18) that cooperates with a projection (28) of said linearly movable member(20), the shape of said hollow profile (18) being such that at least some rotations of said rotary counting wheel (10) result in a linear motion of said linearly movable member (20), changing the position of said linearly movable member (20) in relation to said counting wheel (10).

10. The indicator according to claim 9, in which said rotary counting wheel (10) and said linearly movable member (20) are placed in cover (40) that includes a viewing window (45) which cooperates with the viewing opening (25) of the linearly movable member (20).

11. The indicator according to claim 10, in which the rotary counting wheel (10), the linearly movable member (20), the actuating means (31, 34, 35) and the cover (40) form a unit which can be mounted in a fluid product dispensing device (B).

12. The indicator according to claim 9, in which said indicia (15) are disposed at least partially along a contour of the hollow profile.

13. The indicator according to claim 9, in which the shape of said hollow profile (18) is irregular so that dose indication is progressive.

14. The indicator according to claim 9, in which said hollow profile (18) is at least partially in the shape of a spiral.

15. The indicator according to claim 1, in which said indicia (15) are numbers and/or symbols.

16. The indicator according to claim 1, in which said indicator includes amplification means, with said amplification means converting linear movement (a) of the transmission element (34) into rotary movement of the actuating member (35), the projection in linear motion of said rotary movement being α, where α>1.

17. The dose indicator according to claim 2, wherein the adaptation means is a peg.

18. A fluid product dispensing device (B) that includes a product reservoir (51), a dispensing member (52) mounted on said reservoir (51), and a dose indicator (A) according to claim 1.

19. The device according to claim 18, in which the dose indicator (A) is actuated by the moving part (54) of the dispensing device (B) which is moved during the actuation of the device (B), and which cooperates with the transmission element (34) of said indicator (A).

20. A fluid product dispensing device comprising:
a dose indicator;
a movable part, separate from the dose indicator, for actuating a dispensing member;
a transmission element for transmitting movement of the moving part to the dose indicator; and
adaptation means located between the transmission element and the movable part;
wherein the adaptation means are for adjusting a distance between the movable part and the transmission element during assembly of the fluid product dispensing device to compensate for manufacturing tolerances of the movable part and the transmission element.

21. A fluid product dispensing device comprising:
a dose indicator;
a movable part, separate from the dose indicator, for actuating a dispensing member;
a transmission element for transmitting movement of the moving part to the dose indicator; and
an adjustable peg attached to the transmission element;
wherein the adjustable peg is slidable relative to the transmission element and contacts the movable part during actuation of the dispensing member;
wherein a force required to slide the adjustable peg relative to the transmission element is higher than an actuation force of the dispensing member such that the adjustable peg slides relative to the transmission element during assembly of the fluid product dispensing device so that the adjustable peg compensates for manufacturing tolerances or different actuating strokes of the movable part and the transmission element; and
wherein the adjustable peg does not slide relative to the transmission element during actuation of the dispensing member.

22. The dose indicator according to claim 1, wherein the adaptation device is configured such that the adaptation device is permanently moved during assembly of the fluid product dispensing device to accurately predetermine the distance at rest between the transmission element and the moving part; and
wherein the adaptation device is configured such that the adaptation device is not moved during subsequent actuations of the fluid dispensing device.

23. The fluid product dispensing device according to claim 20, wherein the movable part is configured to force the adaptation means to move relative to the transmission element such that a reduced distance is created between a distal end of the adaptation means and the transmission element; and
wherein the reduced distance does not change during actuation of the dispenser member.

24. The fluid product dispensing device according to claim 21, wherein the movable part is configured to force the adjustable peg to move relative to the transmission element such that a reduced distance is created between a distal end of the adjustable peg and the transmission element; and wherein the reduced distance does not change during actuation of the dispenser member.

25. The indicator according to claim 17, in which, after assembly of the dispensing device, and in the rest position, the peg (134) is located at a distance from the moving part (54) of the dispensing device (B) intended to actuate the indicator (A).

26. A dose indicator (A) for a fluid product dispensing device (B), including at least one rotary counting device (10) capable of being rotated, said at least one counting device including indicia (15) showing the number of doses dispensed or remaining to be dispensed, said at least one counting device being actuated by an actuating member (35) which itself is actuated by a transmission element (34) suitable to cooperate with a moving part (54) of said dispensing device (B) at each actuation of the dispensing device, wherein said dose indicator includes an adaptation device (134) located between said transmission element (34) and said moving part (54) of said dispensing device (B), said adaptation device (134) being deformable, during assembly of the dispensing device (B), thereby setting a distance between said transmission element (34) and said moving part (54) to a predetermined distance when the dispensing device is in a rest position.

27. The fluid product dispensing device according to claim 18, wherein the dispensing member comprises a pump or a valve.

28. The dose indicator according to claim 1, wherein the adaptation device is movable so as to set the position at which the moving part engages the transmission element via the adaptation device during actuation of the fluid product dispensing device.

29. The fluid product dispensing device according to claim 20, wherein the adaptation means is movable and/or deformable so as to set the position at which the movable part engages the transmission element via the adaptation means during actuation of the fluid product dispensing device.

30. The fluid product dispensing device according to claim 21, wherein the adjustable peg is slidable so as to set the position at which the movable part engages the transmission element via the adjustable peg during actuation of the fluid product dispensing device.

31. The dose indicator according to claim 26, wherein the adaptation device is deformable so as to set the position at which the moving part engages the transmission element via the adaptation device during actuation of the fluid product dispensing device.

* * * * *